United States Patent
St. Germain et al.

(10) Patent No.: US 8,304,401 B2
(45) Date of Patent: Nov. 6, 2012

(54) COMPOSITIONS AND METHODS FOR DECREASING TYPE III DEIODINASE ACTIVITY TO MODULATE ADIPOSITY AND BLOOD GLUCOSE LEVELS

(75) Inventors: Donald L. St. Germain, Scarborough, ME (US); Arturo Hernandez, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 13/059,264

(22) PCT Filed: Sep. 1, 2009

(86) PCT No.: PCT/US2009/055597
§ 371 (c)(1),
(2), (4) Date: Feb. 16, 2011

(87) PCT Pub. No.: WO2010/027965
PCT Pub. Date: Mar. 11, 2010

(65) Prior Publication Data
US 2011/0159010 A1    Jun. 30, 2011

Related U.S. Application Data

(60) Provisional application No. 61/093,542, filed on Sep. 2, 2008.

(51) Int. Cl.
  A61K 31/70    (2006.01)
  C07H 21/02    (2006.01)
  C07H 21/04    (2006.01)

(52) U.S. Cl. ............... 514/44 A; 536/23.1; 536/24.5
(58) Field of Classification Search ............... 514/44; 536/24.5, 23.1
See application file for complete search history.

(56) References Cited

U.S. PATENT DOCUMENTS
2003/0228628 A1    12/2003    Powell ................... 435/7.1

FOREIGN PATENT DOCUMENTS
WO    WO 99/55904    11/1999

OTHER PUBLICATIONS

Becker et al. "The Type 2 and Type 3 Iodothyronine Deiodinases Play Important Roles in Coordinating Development in *Rana catesbeiana* Tadpoles" Endocrinology 1997 138(7):2989-2997.
Bianco et al. "Biochemistry, Cellular and Molecular Biology, and Physiological Roles of the Iodothyronine Selendeiodinases" Endocrine Reviews 2002 23(1):38-89.
Darras et al. "Effects of Dexamethasone Treatment on Iodothyronine Deiodinase Activities and on Metamorphosis-related Morphological Changes in the Axolotl (*Ambystoma mexicanum*)" General and Comparative Endocrinology 2002 127(2):157-164.

(Continued)

*Primary Examiner* — Terra Cotta Gibbs
(74) *Attorney, Agent, or Firm* — Licata & Tyrrell P.C.

(57) ABSTRACT

The present invention features methods for decreasing fat mass, increasing energy expenditure, increasing resistance to obesity, and lowering blood glucose levels in a subject with an agent that inhibits the expression or activity of type III deiodinase. In this regard, agents of the invention are useful in treating diabetes and obesity.

16 Claims, 3 Drawing Sheets

OTHER PUBLICATIONS

Dentice et al. "Sonic Hedgehog-induced Type 3 Deiodinase Blocks Thyroid Hormone Action Enhancing Proliferation of Normal and Malignant Keratinocytes" Proceedings of the National Academy of Sciences 2007 104(36):14466-14471.

Hernandez, A. and St. Germain, D.L. "Dexamethasone Inhibits Growth Factor-Induced Type 3 Deiodinase Activity and mRNA Expression in a Cultured Cell Line Derived from Rat Neonatal Brown Fat Vascular-Stromal Cells" Endocrinology 2002 143(7):2652-2658.

Hernandez et al. "Type 3 Deiodinase is Critical for the Maturation and Function of the Thyroid Axis" The Journal of Clinical Investigation 2006 116(2):476-484.

Hernandez et al. "Type 3 Deiodinase Deficiency Results in Functional Abnormalities at Multiple Levels of the Thyroid Axis" 2007 148(12):5680-5687.

Sanders et al. "Cloning and Characterization of Type III Iodothyronine Deiodinase from the Fish *Oreochromis niloticus*" Endocrinology 1999 140(8):3666-3673.

St. Germain et al. "Insights Into the Role of Deiodinases from Studies of Genetically Modified Animals" Thyroid 2005 15(8):905-916.

Villicev et al. "Thyroid Hormone Receptor β-specific Agonist GC-1 Increases Energy Expenditure and Prevents Fat-mass Accumulation in Rats" Journal of Endocrinology 2007 193(1):21-29.

COMPOSITIONS AND METHODS FOR DECREASING TYPE III DEIODINASE ACTIVITY TO MODULATE ADIPOSITY AND BLOOD GLUCOSE LEVELS

This patent application is the National Stage of International Application No. PCT/US2009/055597 filed Sep. 1, 2009 and claims the benefit of priority of U.S. Provisional Application No. 61/093,542, filed Sep. 2, 2008, the content of which is incorporated herein by reference in its entirety.

This invention was made with government support under grant number ROI DK-54716-1 awarded by the National Institutes of Health. The government has certain rights in the invention.

BACKGROUND OF THE INVENTION

Although thyroxine (tetraiodothyronine; $T_4$) is the principal secretory product of the vertebrate thyroid, its essential metabolic and developmental effects are primarily mediated by 3,3,5-triiodothyronine ($T_3$), which is produced from the prohormone by 5'-deiodination. The type I iodothyronine deiodinase (D1), a thiol-requiring propylthiouracil-sensitive oxidoreductase, is found mainly in liver and kidney and catalyzes conversion of $T_4$ to $T_3$ by a deiodination reaction at the outer ring of $T_4$ and conversion of 3,3',5'-triiodothyronine (reverse T3, $rT_3$) to 3,3'-diiodothyronine (T2). Two other deiodinases have also been described, type II deiodinase (D2) and type III deiodinase (D3). The action of D2 is similar to D1; however, D2 is primarily found in the thyroid, pituitary gland, brain, brown fat and testis. In contrast to D1 and D2, D3 functions exclusively as a 5-deiodindinase and catalyzes the conversion of T4 and T3 to inactive metabolites (rT3 and T2, respectively) and is primarily found in fetal tissues, placenta, skin and brain as well as brown and white preadipocytes. See Bianco, et al. (2002) *Endocrine Rev.* 23:38-89.

By targeted inactivation of the D3 gene in mouse embryonic stem cells, D3-knockout mice have been generated and shown to exhibit neonatal thyrotoxicosis followed later by persistent central hypothyroidism (Hernandez, et al. (2006) *J. Clin. Invest.* 116: 476-484). Early in life, the mutant mice have delayed T3 clearance, markedly elevated serum T3 levels, and overexpression of T3-inducible genes in the brain. From postnatal day 15 through adulthood, D3-knockout mice exhibit central hypothyroidism, with low serum levels of T4 and T3, and modest or no increase in thyroid-stimulating hormone concentration; peripheral tissues are also hypothyroid. Hypothalamic T3 content is decreased, whereas thyrotropin-releasing hormone expression is elevated. Furthermore, treatment of D3-knockout mice with T3 results in weight loss and lethality in mutant animals (Hernandez, et al. (2007) *Endocrinology* 148:5680-5687). Based upon these results, it has been concluded that D3 plays a critical role in the maturation and function of the thyroid axis.

D3 expression in a brown fat vascular-stromal (BVS-1) cell line has been shown to be regulated by growth factors such as EGF, acid or basic FGF, wherein preincubation of cells overnight with dexamethasone completely blocks the D3-inducing effects of basic FGF and decreased basal D3 activity by 80% (Hernandez & Germain (2002) *Endocrinology* 143: 2652-2658). Similarly, acute or chronic treatment of neotenic axolotls (*Ambystoma mexicanum*) with dexamethasone has been shown to decrease hepatic and renal D3 activity in a dose-dependent manner, with all dexamethasone-treated axolotls showing a clear reduction in gill length, tail height, and body weight (Darras, et al. (2002) *Gen. Comparat. Endocrinol.* 127:157-164)

SUMMARY OF THE INVENTION

The present invention features methods for decreasing fat mass, increasing energy expenditure, increasing resistance to obesity, and lowering blood glucose levels in a subject by administering to a subject in need of treatment an effective amount of an agent that decreases the expression or activity of type III deiodinase. According to particular embodiments, the subject being treated is human. In other embodiments the agent is selective for type III deiodinase. In alternative embodiments, the agent is an antisense, siRNA, siRNA-like, or ribozyme molecule; or iopanoic acid, iodoacetate or an antagonistic antibody or antibody fragment.

DETAILED DESCRIPTION OF THE INVENTION

Figure 1:
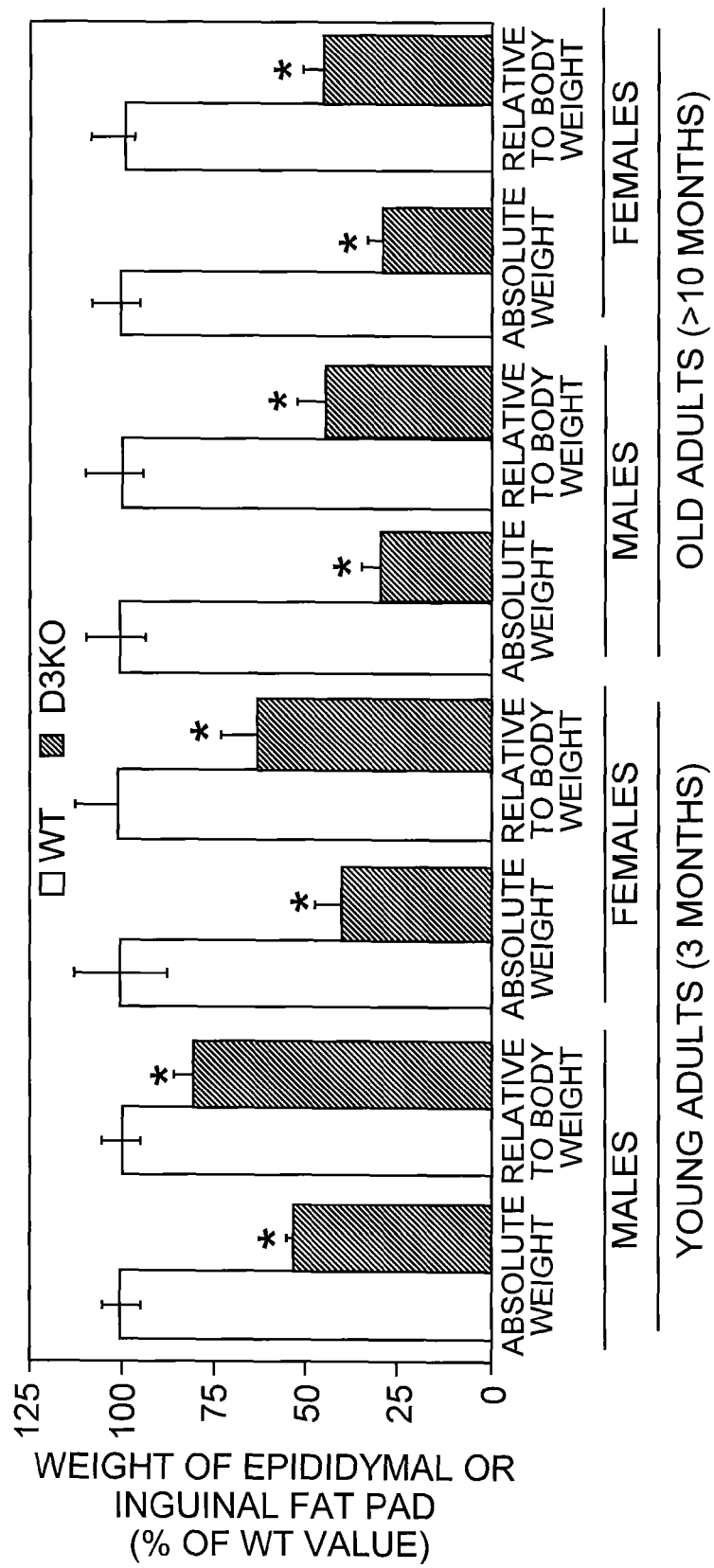
FIG. 1 shows the weight of the epididymal (males) and parametrial (females) fat pad in young and old mice deficient in D3 expression (D3KO) of both sexes compared to wild-type (WT) animals (n=9 to 31).

It has now been shown that D3 plays an important role in regulating body fat content via its ability to alter local tissue concentrations of thyroid hormone. Using a mouse model deficient in D3 expression, it has now been shown that decreased D3 levels result in decreased fat mass, increased energy expenditure, increased resistance to obesity, and lowering of blood glucose levels. Thus, the present invention embraces the manipulation of D3 expression or activity during development and/or adulthood to reduce adiposity, raise basal metabolic rate, prevent obesity and improve glucose control in patients with diabetes.

In the context of the present invention, D3 or type III deiodinase is a protein belonging to the iodothyronine deiodinase family that catalyzes the inactivation of thyroid hormone by inner ring deiodination of the prohormone thyroxine ($T_4$) and the bioactive hormone 3,3',5-triiodothyronine ($T_3$) to inactive metabolites, 3,3',5'-triiodothyronine ($rT_3$) and 3,3'-diiodothyronine ($T_2$), respectively. The D3 protein contains a selenocysteine (Sec) residue, which is essential for efficient enzyme activity. The selenocysteine is encoded by the UGA codon, which normally signals translation termination. The 3'-untranslated region of Sec-encoding mRNAs have a common stem-loop structure, the Sec insertion sequence, which is necessary for the recognition of UGA as a Sec codon rather than as a stop signal. Nucleic acid molecule encoding D3 are well-known in the art and set forth, for example, in GENBANK Accession Nos. NM_001362 (human), AK140797 (mouse), NM_017210 (rat), NP_001010993 (Bos taurus) and NP_001081332 (*Xenopus* laevis), each incorporated herein by reference. Likewise, the amino acid sequences of D3 enzymes are well-known in the art and set forth, for example, in GENBANK Accession Nos. NP_001353 (human), NP_742117 (mouse), NP_058906 (rat), NM_001010993 (*Bos taurus*) and NM_001087863 (*Xenopus laevis*), each incorporated herein by reference.

In accordance with the methods of the present invention, D3 levels are decreased or reduced using an agent which inhibits the expression or activity of D3. In this regard, agents of the invention, also referred to herein as D3 inhibitory agents, can be proteins, antibodies, antibody fragments, aptamers, peptides, nucleic acids, oligonucleotides, siRNA, ribozymes, carbohydrates, lipids, synthetic or semi-synthetic molecules, or purified natural products.

By way of illustration, D3 expression can be inhibited using a siRNA or siRNA-like molecule which specifically binds to a D3-encoding nucleic acid (e.g., GENBANK Accession No. NM_001362, AK140797, NM_017210, NP_001010993 or NP_001081332) or a fragment thereof. A siRNA-like molecule refers to a nucleic acid molecule similar to a siRNA (e.g., in size and structure) and capable of eliciting siRNA activity, i.e., to effect the RNAi-mediated inhibition of expression. Inhibitory RNAs can be specific for sequences in the 5', 3' or middle of the RNA molecule, wherein target regions can be selected experimentally or empirically. For example, siRNA target sites in a gene of interest can be 19-27 nucleotides in length, include an AA dinucleotide sequence at the 5' end and preferably have a G/C content of 30-50% (see, e.g., Elbashir, et al. (2001) *Nature* 411: 494-498). Kits for production of dsRNA for use in RNAi are available commercially, e.g., from New England Biolabs, Inc. and Ambion Inc. (Austin, Tex., USA). Methods of transfection of dsRNA or plasmids engineered to make dsRNA are routine in the art. An exemplary D3 shRNAi oligonucleotide is 5'-TCG ACG TTG ACT TCC TTA TCA TCC-3' (SEQ ID NO:1), which maps to nucleotides 490-510 of mouse D3 cDNA (see, e.g., Dentice, et al. (2007) *Proc. Natl. Acad. Sci. USA* 104(36):14466-14471).

By way of further illustration, the D3 expression can be inhibited by an antisense molecule or a ribozyme. Ribozyme catalysis has primarily been observed as part of sequence-specific cleavage/ligation reactions involving nucleic acids (Joyce (1989) *Nature* 338:217). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression can be particularly suited to therapeutic applications (Scanlon, et al. (1991) *Proc. Natl. Acad. Sci. USA* 88:10591; Sarver, et al. (1990) *Science* 247:1222; Sioud, et al. (1992) *J. Mol. Biol.* 223:831). Therefore, in particular embodiments, the invention embraces antisense molecules, siRNA or siRNA-like molecules, or ribozymes for promoting the selective degradation of D3 mRNA or inhibition of D3 protein translation thereby decreasing or reducing D3 levels.

A decrease in D3 activity can also be achieved using a D3 antagonistic antibody or antibody fragment, which, e.g., selectively blocks binding of D3 to its substrate. Methods for generating such antibodies or antibody fragments and methods for screening for antagonistic activity (e.g., via assays measuring the conversion of $T_4$ to $rT_3$ or the conversion of $T_3$ to 3,3'-$T_2$) are routinely practiced in the art. Such antibodies can be either polyclonal or monoclonal. Moreover, such antibodies can be natural or partially or wholly synthetically produced. All fragments or derivatives thereof (e.g., Fab, Fab', F(ab')$_2$, scFv, Fv, or Fd fragments) which maintain the ability to specifically bind to and inhibit D3 activity are also included. The antibodies can be a member of any immunoglobulin class, including any of the human classes: IgG, IgM, IgA, IgD, and IgE.

D3-specific antibodies can be generated using classical cloning and cell fusion techniques. See, for example, Kohler and Milstein (1975) *Nature* 256:495-497; Harlow and Lane (1988) *Antibodies: A Laboratory Manual*, Cold Spring Harbor Laboratory, New York. Alternatively, antibodies which specifically bind D3 are derived by a phage display method. Methods of producing phage display antibodies are well-known in the art (e.g., Huse, et al. (1989) *Science* 246(4935): 1275-81).

Selection of D3-specific antibodies is based on binding affinity and can be determined by various well-known immunoassays including, enzyme-linked immunosorbent, immunodiffusion chemiluminescent, immunofluorescent, immunohistochemical, radioimmunoassay, agglutination, complement fixation, immunoelectrophoresis, and immunoprecipitation assays and the like which can be performed in vitro, in vivo or in situ. Such standard techniques are well-known to those of skill in the art (see, e.g., "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984) *J. Clin. Chem. Clin. Biochem.* 22:895-904). Once fully characterized for specificity, the antibodies of the invention can be assayed for their ability to antagonize D3 activity in D3 enzymatic assays.

Agents of the invention also include organic compounds which have been shown to inhibit D3 activity. For example, iodinated radiographic contrast agents such as iopanoic acid (Becker, et al. (1997) *Endocrinology* 138(7):2989-97; Bianco, et al. (2002) supra) effectively inhibit D3 activity. Similarly, iodoacetate exhibits D3 inhibitory activity (Sanders, et al. (1999) *Endocrinology* 140(8):3666-73).

In addition to those specifically disclosed herein, additional D3 inhibitors can be identified by the generation of analogs or derivatives of known inhibitors, which can be used as lead compounds. By way of illustration of how inhibitors can be identified that selectively inhibit one of the deiodinases, gold thioglucose (GTG) is a competitive inhibitor of both D3-catalyzed $T_3$ 5 deiodination and D1-catalyzed $rT_3$ deiodination. However, the difference in Ki with regard to these two inhibitory activities is approximately 1000-fold, with D1 being much more sensitive to inhibition than is D3 (Ki 6 nM vs 5.2 µM, respectively). Based upon such differences, lead compounds can be generated that have excellent specificity for specific deiodinases.

In addition to the modification of lead compounds, libraries of compounds containing pure agents or collections of agent mixtures can be screened for D3 inhibitory activity. Examples of pure agents include, but are not limited to, proteins, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, one may not only identify those crude mixtures that possess the desired activity, but also monitor purification of the active component from the mixture for characterization and development as a therapeutic drug. In particular, the mixture so identified may be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction may be assayed for the desired activity using the original assay until a pure, biologically active agent is obtained.

Library screening can be performed in any format that allows rapid preparation and processing of multiple reactions such as in, for example, multi-well plates of the 96-well variety. Stock solutions of the agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, luminometers, spectrophotomers, calorimeters, and fluorimeters, and devices that measure the decay of radioisotopes. It is contemplated that any suitable D3 enzymatic assay can be used including monitoring the conversion of $T_4$ to $rT_3$ or the conversion of $T_3$ to $3,3'-T_2$ in the presence or absence of a test agent.

In particular embodiments of the present invention, a D3 inhibitor agent is selective for D3. A selective D3 inhibitor is an agent, which inhibits D3 to a greater extent (e.g., a lower $K_i$) than it inhibits D2 or D1 enzymes. A selective D3 inhibitor also includes agents that inhibit D3, but fail to inhibit D2 or D1 at comparable concentrations.

D3 inhibitory agents disclosed herein find application in methods for decreasing fat mass, increasing energy expenditure, increasing resistance to obesity, and lowering blood glucose levels. Generally, such methods involve administering to a subject in need of treatment a D3 inhibitory agent in an amount that effectively reduces the level or activity of D3 by at least 50%, 60%, 70%, 80%, 90%, 95%, 99% or 100%. Subjects benefiting from treatment with an agent of the invention include obese subjects, subjects at risk of obesity (e.g., subjects consuming a high fat diet or having a genetic predisposition to obesity), or subjects with or at predisposed to have diabetes. In the context of this invention, a subject can be any mammal including human, companion animals (e.g., dogs or cats), livestock (e.g., cows, sheep, pigs, or horses), or zoological animals (e.g., monkeys). In particular embodiments, the subject is a human.

While particular embodiments of this invention embrace in vivo applications, in vitro and ex vivo use of agents of the invention are also contemplated for examining the effects of D3 and thyroid hormones on proliferation, differentiation, and metabolic status of cultured brown fat and white fat precursor cells. In addition to treatment, agents of the invention also find application in monitoring the phenotypic consequences (e.g., basal metabolic rate, propensity for obesity, effect on insulin resistance and development of diabetes) of D3 deficiency in mouse models of obesity and diabetes.

When used in therapeutic applications, a D3 inhibitor of the invention will have the therapeutic benefit of decreasing fat mass, increasing energy expenditure, increasing resistance to obesity, and/or lowering blood glucose levels in a subject as compared to subjects not receiving treatment with the D3 inhibitor. A D3 inhibitor of the invention is expected to decrease fat mass (e.g., the weight of fat as a percent of total body weight) or increase energy expenditure (e.g., as determined by basal metabolic rate) in a subject by at least 10%, 20%, 30%, 40%, 50%, 60%, 70%, or 80%. Based upon the data presented herein, the decrease in fat mass or increase in energy expenditure can be dependent on factors such as age and sex of the subject, wherein older subjects may benefit more than younger subjects and women may benefit more than men.

When employed in a method for increasing resistance to obesity, it is expected that an agent of the invention can, e.g. reduce weight gain of a subject by 10%, 20%, 30%, 40%, 50%, 60% 70%, 80% or 90% compared to a subject consuming the same diet, but not receiving a D3 inhibitory agent. In so far as D3 deficiency enhances the utilization of calories in a subject, use of the agents of this invention can be particularly beneficial in subjects having a tendency toward high fat diets or subjects with a predisposition for being obese.

As indicated, a D3 inhibitory agent of the invention also finds application in a method for lowering blood glucose levels in a subject. It is expected that a subject receiving a D3 inhibitor will exhibit a fasting blood glucose level at least 10%, 20%, 30%, 40% or 50% lower than a subject not receiving the D3 inhibitor. In this regard, agents of the invention are useful in preventing or treating diabetes and improving glucose tolerance.

Successful clinical use of a D3 inhibitory agent can be determined by the skilled clinician or veterinarian based upon routine clinical practice, e.g., by monitoring fat mass, basal metabolic rate, weight gain, and blood glucose levels according to methods known in the art.

For therapeutic use, D3 inhibitory agents can be formulated with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Compositions of the present invention can be administered parenterally (for example, by intravenous, intraperitoneal, subcutaneous or intramuscular injection), topically (including buccal and sublingual), orally, intranasally, intravaginally, or rectally according to standard medical practices.

The selected dosage level will depend upon a variety of factors including the activity of the particular agent of the present invention employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and other factors well-known in the medical arts.

A physician or veterinarian having ordinary skill in the art can readily determine and prescribe the effective amount of the pharmaceutical composition required based upon the administration of similar compounds or experimental determination. For example, the physician or veterinarian could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

The invention is described in greater detail by the following non-limiting examples.

EXAMPLE 1

D3 as a Modulator of Adiposity and Blood Glucose Level

Figure 2:
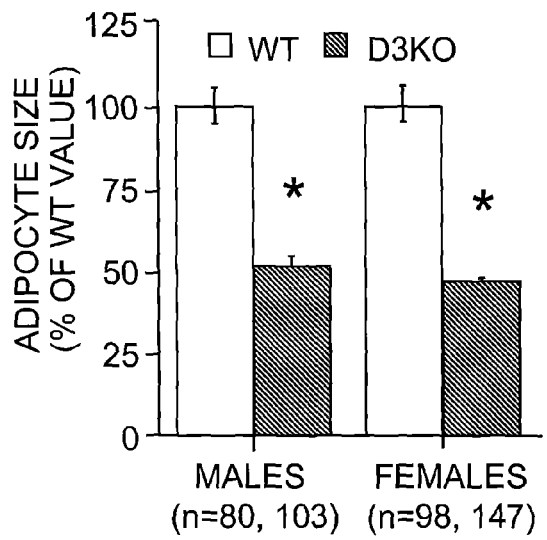
FIG. 2 shows quantification of adipocyte size in wild-type (WT) and D3-deficient mice (D3KO).
Figure 3A:
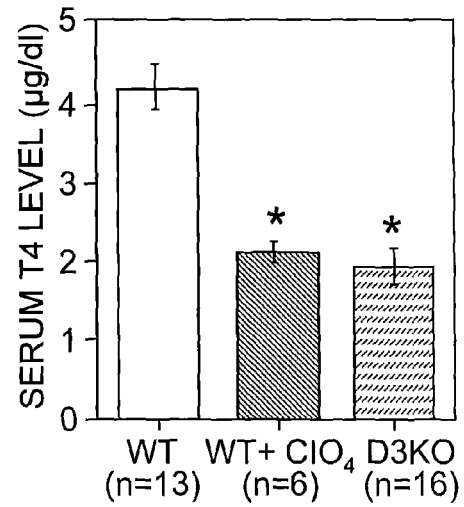
FIG. 3 shows serum thyroid hormone levels (FIGS. 3A and 3B) and relative weight of epididymal fat pad (FIG. 3C) in wild-type (WT) and D3-deficient mice (D3KO) as compared to wild-type mice treated for two months with 0.04% perchlorate ($ClO_4$) to render the animals hypothyroid.
Figure 3B:
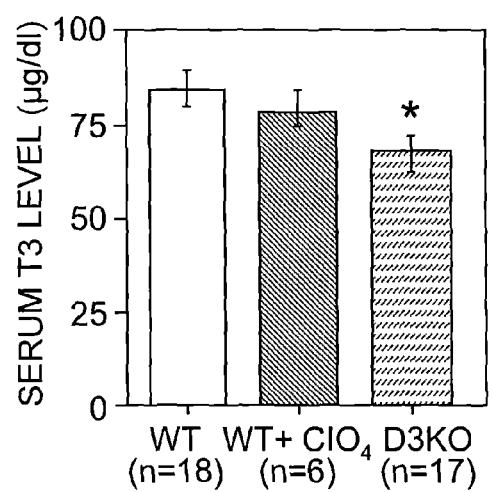
Figure 3C:
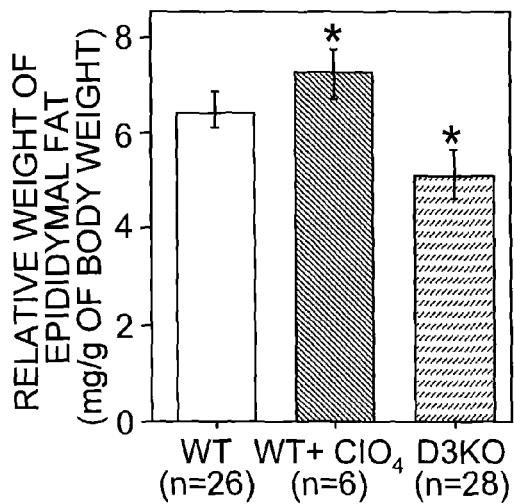

To demonstrate the role of the D3 in regulating fat mass and energy homeostasis, adiposity parameters in wild-type and D3-deficient (D3KO) mice were evaluated. Analysis of relative weights (compared to total body weight) of male epididymal (EPI) and female parametrial white adipose tissue (WAT) indicated a significant reduction in adult D3KO mice (20% reduction in males and 35% in females, $P<0.001$, see FIG. 1). This reduction was more marked in aged D3KO mice (60%, $P<0.001$). Histological analysis revealed that white adipocyte size was reduced 50% in D3KO mice ($P<0.001$, FIG. 2). These alterations were not due to the moderate hypothyroidism present in the D3KO mouse, as wild-type mice made hypothyroid with 0.04% perchlorate to a degree similar to that in D3KO mice manifested a 15% increase in EPI WAT weight ($P<0.01$, FIG. 3). Thus, the decreased adiposity of the D3KO mouse is both unexpected and even more striking in degree.

Figure 4A:
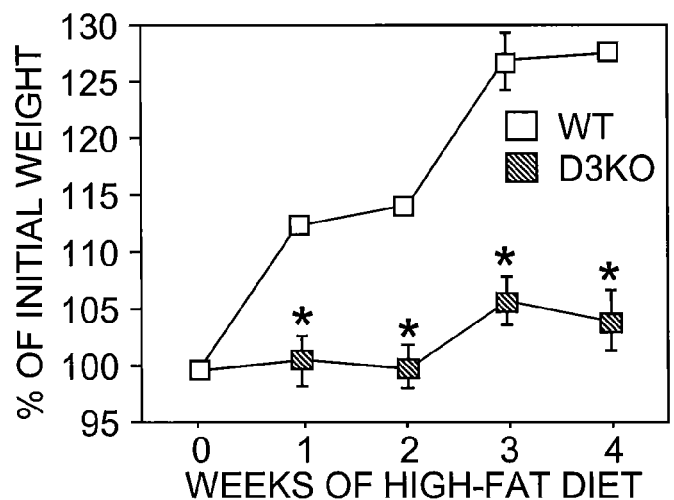
FIG. 4 shows the percentage of weight gain (FIG. 4A), weight of epididymal fat (FIG. 4B) and food consumption (FIG. 4C) in wild-type (WT) and D3-deficient mice (D3KO) fed a high-fat diet for four weeks (WT, n=5; D3KO, n=6).
Figure 4B:
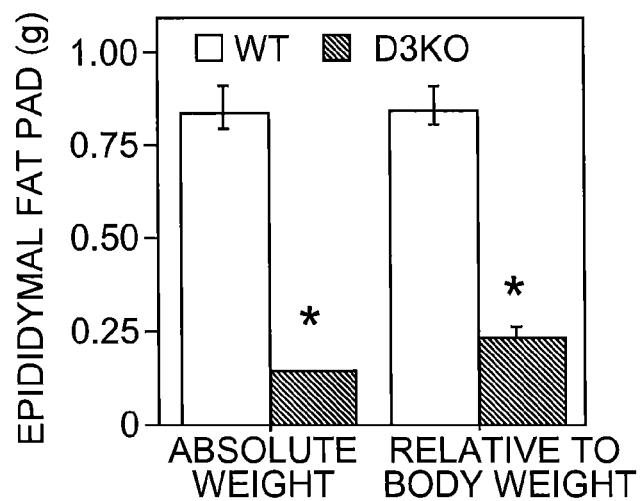
Figure 4C:
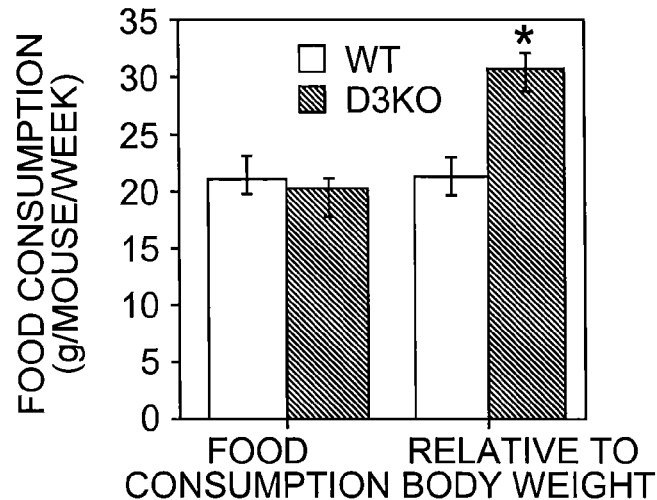

When wild-type and D3KO mice were fed a high fat diet, they gained, respectively, 25% and 5% in total weight ($P<0.001$, FIG. 4A), and 450% and 50% in EPI WAT weight ($P<0.001$, FIG. 4B). D3KO mice, although 35% smaller than wild-type animals, consumed the same amount of food as wild-type mice, whether it was a normal or a high fat diet (FIG. 4C). Thus, the lesser degree of weight gain in the D3KO mouse was not a result of decreased food consumption. Unexpectedly, given their modestly hypothyroid state, the basal metabolic rate was observed to be 22% higher in D3KO mice than in wild-type mice ($P<0.005$). Indeed, at three to five months of age, wild-type mice (n=5) exhibited a basal metabolic rate of 50.4±0.3 L/Kg/day, while in D3KO mice (n=5) this parameter was 61.4±1.8 ($P<0.005$). Additional data indicated that the increase in BMR also pertains to aged (20 month-old) mice. This observation of an increased basal metabolic rate in the D3KO mouse explains the reduced adiposity, diet-induced resistance to obesity and increased relative food intake that were observed in the D3KO animals, and indicates that central regulatory mechanisms of energy balance are affected by D3 deficiency.

Additional observations indicate that the D3KO mouse exhibited a significantly lower fasting blood glucose level than that observed in wild-type mice. After an overnight fasting, the blood glucose in young, wild-type male mice (3 to 4 months of age) was 80.3±1.9 mg/dL (n=10), whereas it was only 57.5±3.1 in D3KO mice (n=11, $P<0.0001$). A similar observation was found in aged male mice (18 to 22 months of age). In this case, blood glucose was 68.3±3.1 mg/dL in wild-type mice (n=18) vs 54.7±4.4 mg/dL in D3KO mice (n=11, $P=0.016$). These finding further indicate that a deficiency of D3 enhances the utilization of calories by the organism.

In addition to its role in the regulation of adiposity, D3 was also found to be highly expressed in proliferating brown fat precursor cells and was highly responsive to epidermal and fibroblast growth factors. This observation was also found in progenitor cells of white adipose tissue (WAT) as they exhibited comparable high D3 activity (8,246±798 fmol/h/mg of protein, n=6) when grown in primary culture. Thyroid hormones are known to have important effects on adipocyte differentiation and function, and it is contemplated that a deficiency of D3, by raising T3 levels within adipocyte precursor cells, promotes premature termination of adipocyte proliferation and thus leads to a lesser fat mass.

Taken together these results indicate that the manipulation of D3 expression or activity can alter metabolic processes that impact on fat mass and the blood glucose level. Specifically, based on these data, it is expected that inhibition of D3 results in reduced adiposity, increased metabolic rate, resistance to obesity, and lower blood glucose levels, likely due to alterations in thyroid hormone action in specific cells and tissues during development and/or in the adult animal in the hypothalamus and/or adipose tissue.

What is claimed is:

1. A method for decreasing fat mass in a subject comprising administering to a subject in need of treatment an effective amount of an agent that decreases the expression or activity of type III deiodinase thereby decreasing fat mass in the subject, wherein the agent is an antisense, siRNA, siRNA-like, or ribozyme molecule.

2. The method of claim 1, wherein fat mass is decreased by at least 10%.

3. The method of claim 1, wherein the subject is human.

4. The method of claim 1, wherein the agent is selective for type III deiodinase.

5. A method for increasing energy expenditure in a subject comprising administering to a subject in need of treatment an effective amount of an agent that decreases the expression or activity of type III deiodinase thereby increasing energy expenditure in the subject, wherein the agent is an antisense, siRNA, siRNA-like, or ribozyme molecule.

6. The method of claim 5, wherein energy expenditure is increased by at least 10%.

7. The method of claim 5, wherein the subject is human.

8. The method of claim 5, wherein the agent is selective for type III deiodinase.

9. A method for increasing resistance to obesity in a subject comprising administering to a subject in need of treatment an effective amount of an agent that decreases the expression or activity of type III deiodinase thereby increasing resistance to obesity in the subject, wherein the agent is an antisense, siRNA, siRNA-like, or ribozyme molecule.

10. The method of claim 9, wherein resistance to obesity is increased by reducing weight gain of the subject by at least 10%.

11. The method of claim 9, wherein the subject is human.

12. The method of claim 9, wherein the agent is selective for type III deiodinase.

13. A method for lowering blood glucose levels in a subject comprising administering to a subject in need of treatment an effective amount of an agent that decreases the expression or activity of type III deiodinase thereby lowering blood glucose levels in the subject, wherein the agent is an antisense, siRNA, siRNA-like, or ribozyme molecule.

14. The method of claim 13, wherein blood glucose levels in the subject are decreased by at least 10%.

15. The method of claim 13, wherein the subject is human.

16. The method of claim 13, wherein the agent is selective for type III deiodinase.

* * * * *

SEQUENCE LISTING

```
<160> NUMBER OF SEQ ID NOS: 1

<210> SEQ ID NO 1
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 1
tcgacgttga cttccttatc atcc                                          24
```